United States Patent [19]

Bregman et al.

[11] Patent Number: 4,718,406
[45] Date of Patent: Jan. 12, 1988

[54] FIBER OPTICS IMAGE SCOPE (MICRO-ENDOSCOPE), URETEROSCOPE

[75] Inventors: Robert U. Bregman; Parviz Soltan, both of San Diego, Calif.

[73] Assignee: The United States of America as represented by the Secretary of the Navy, Washington, D.C.

[21] Appl. No.: 392,185

[22] Filed: Jun. 28, 1982

[51] Int. Cl.⁴ .............................................. A61B 1/06
[52] U.S. Cl. ........................................................ 128/6
[58] Field of Search ........................................ 128/4–8

[56] References Cited

U.S. PATENT DOCUMENTS

| | | | |
|---|---|---|---|
| 1,453,975 | 5/1923 | Greenberg et al. | 128/7 |
| 3,074,408 | 1/1963 | Chester | 128/7 |
| 3,279,460 | 10/1966 | Sheldon | 128/6 |
| 3,417,745 | 12/1968 | Sheldon | 128/6 |
| 3,437,747 | 4/1969 | Sheldon | 128/6 |
| 3,481,660 | 12/1969 | Sheldon | 350/96 |
| 3,572,325 | 3/1971 | Bazell | 128/6 |
| 3,792,701 | 2/1974 | Kloz et al. | 128/7 |
| 3,886,933 | 6/1975 | Mori et al. | 128/7 |
| 3,889,662 | 6/1975 | Mitsui | 128/6 |
| 3,960,143 | 6/1976 | Terada | 128/4 |
| 4,146,019 | 3/1979 | Bass et al. | 128/6 |
| 4,204,528 | 5/1980 | Termanini | 128/6 |
| 4,248,214 | 2/1981 | Hannah et al. | 128/7 |
| 4,361,139 | 11/1982 | Takagi | 128/6 |

OTHER PUBLICATIONS

Uretero-Penoscope, 12 Mar. 1985, Castro.
The Urologic Clinics of North America, vol. 9, No. 1, Feb. 1982, Smith.
Endoscopy: Developments in Optical Instrumentation Science, vol. 210, 17 Oct. 1980, Epstein.

*Primary Examiner*—Kyle L. Howell
*Assistant Examiner*—Max F. Hindenburg
*Attorney, Agent, or Firm*—Robert F. Beers; Ervin F. Johnston; Thomas Glenn Keough

[57] ABSTRACT

An endoscope of such small size and flexibility to allow safe diagnosis and treatment of lesions and disorders of the ureter and kidney. A 2mm outer diameter tube fabricated from a low friction material includes a bundle of fiber optics shaped to conform to an inner sector of the tube. This bundle provides illumination while a second fiber optic bundle, bonded alongside the first bundle, permits observation at a distal end. The remainder of the interior of the tube defines a longitudinal duct for the bidirectional exchange of fluids. The internal disposition of the fiber bundles and duct keeps the dimensions small enough to permit ureteral and renal applications as well as other heretofore inaccessible places.

3 Claims, 3 Drawing Figures

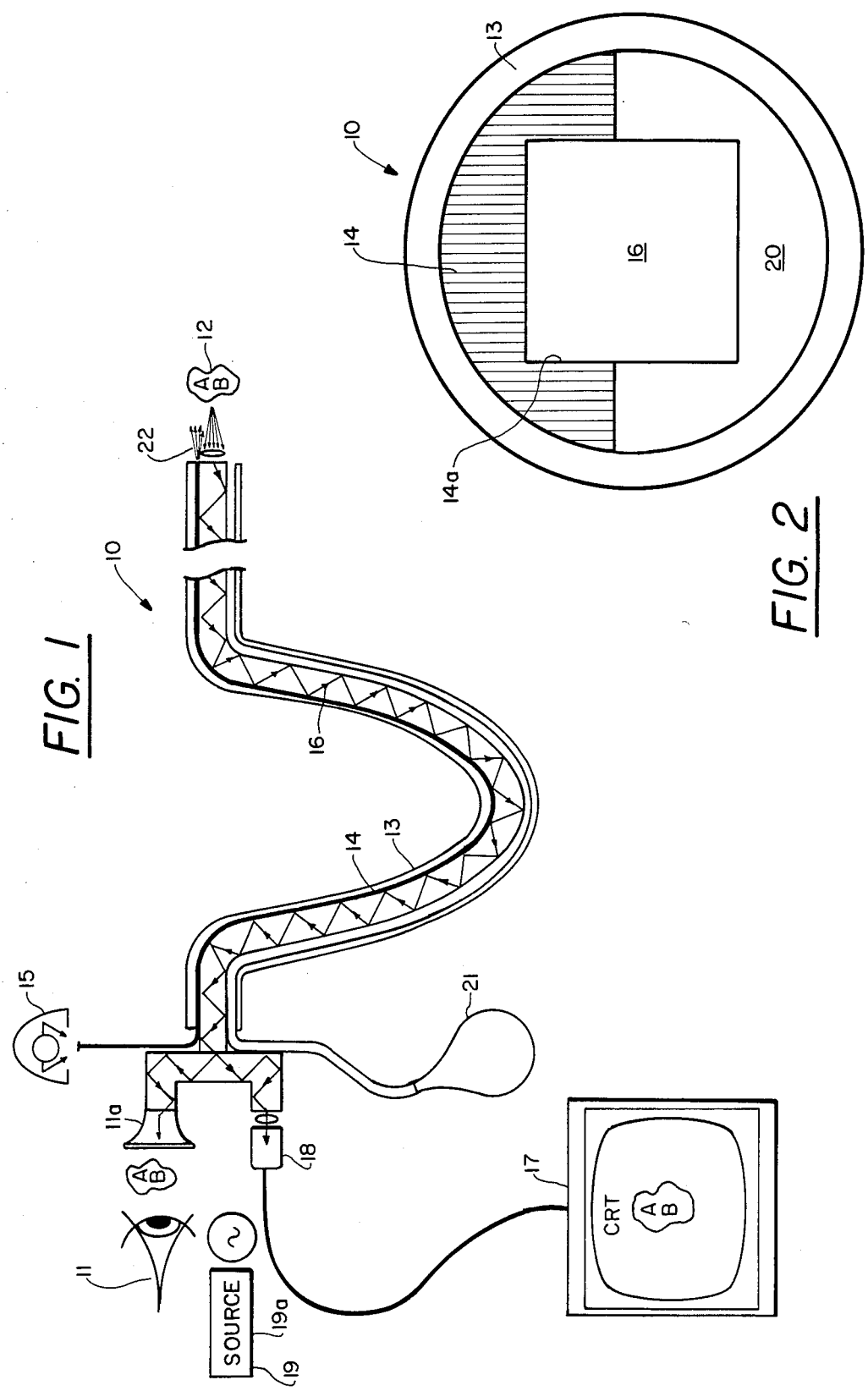

FIBER OPTICS IMAGE SCOPE (MICRO-ENDOSCOPE), URETEROSCOPE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The advent of fiber optics has provided an opportunity for miniaturization and refinement of medical endoscopic tools for cardiopulmonary, orthopedic, gastroenterologic, gynecologic, urologic, and general surgical applications. The evolution of design continues to aid in the diagnosis and treatment of a variety of disorders.

An endoscope by Masaaki Terada as described in U.S. Pat. No. 3,960,143 discloses an endoscope that permits the passage of medical instruments for a surgical operation. The multilayered tubes have low frictional coefficient materials for transmission of instruments within an outer flexible tube. The overall diameter of the endoscope appears to be in the neighborhood of 20 millimeters.

A later design by Michael Bass et al in U.S. Pat. No. 4,146,019 provides for the removal of blood clots and the like while observing an operation. Their endoscope has a number of internal channels for illuminating, viewing, flushing, evacuating and operating. The many features of the Bass et al endoscope make the diameter dimension in the neighborhood of one-half inch.

A still later design by Termanini in U.S. Pat. No. 4,204,528 permits the illumination or selected portions of the cardiovascular system and the injecting of a clear fluid for observation purposes. An extendable and retractable irrigation head passes a clear solution to reduce the opacity of the blood and thereby increases the diagnostic capabilities of physicians. The outside diameter of the catheter is approximately eight millimeters.

Thus, there is an unmet need in the state-of-the-art for an endoscope having a reduced diameter and flexibility in the neighborhood of two millimeters to allow the diagnosis and treatment of ureteral and renal disorders.

SUMMARY OF THE INVENTION

The invention is directed to providing an improved flexible endoscope for diagnosing and treating a patient. A first bundle of fiber optics extends the length of the endoscope for providing illumination and has a sector-shaped cross-sectional configuration. A second bundle of fiber optics extends the length of the endoscope and is secured to the first bundle for permitting observation. A single elongate flexible tubing has an outer dimension of two millimeters for encasing the first bundle of illuminating fiber optics and the second bundle of observation-permitting fiber optics and for defining a longitudinal fluid duct that completely fills the remainder of the tube. Thusly fabricated, a reduced dimension flexible endoscope is capable of aiding in the diagnosis and the treatment of ureteral and renal disorders.

It is a prime object of the invention to provide an improvement for endoscopes.

Still another object is to provide an endoscope that is cost-effective allowing a low risk diagnosis and treatment of benign and malignant lesions of the ureter or renal collection system.

Still another object is to provide a reduced size endoscope capable of being rapidly employed to give access to previously inaccessible locations in the body.

Still another object is to provide an endoscope fabricated of a tubing containing two fiber optic bundles that create a sufficient size bidirectional duct.

Still another object is to provide a unitized endoscope construction affording a brilliant image, ease of sterilization and durability.

Still another object is to provide an endoscope of small size and flexibility to allow the viewing of the human ureter and kidney.

Another object is to provide an alternative, safe method of diagnosis and treatment of ureteral and renal collecting system disorders without resorting to open surgery.

A further object of the invention is to minimize use of X-radiation for diagnosis.

Yet another object is to minimize risk of allergic reaction to intravenous contrast material for urography.

These and other objects of the invention will become more readily apparent from the ensuing specification and claims when taken with the drawings.

BRIEF DESCRIPTION OF THE DRAWINGS

FIG. 1 is a cross-sectional schematic representation of a preferred form of this inventive concept.

FIG. 2 shows a lateral cross-sectional view of a preferred form of the invention.

DESCRIPTION OF THE PREFERRED EMBODIMENT

Figure 3:
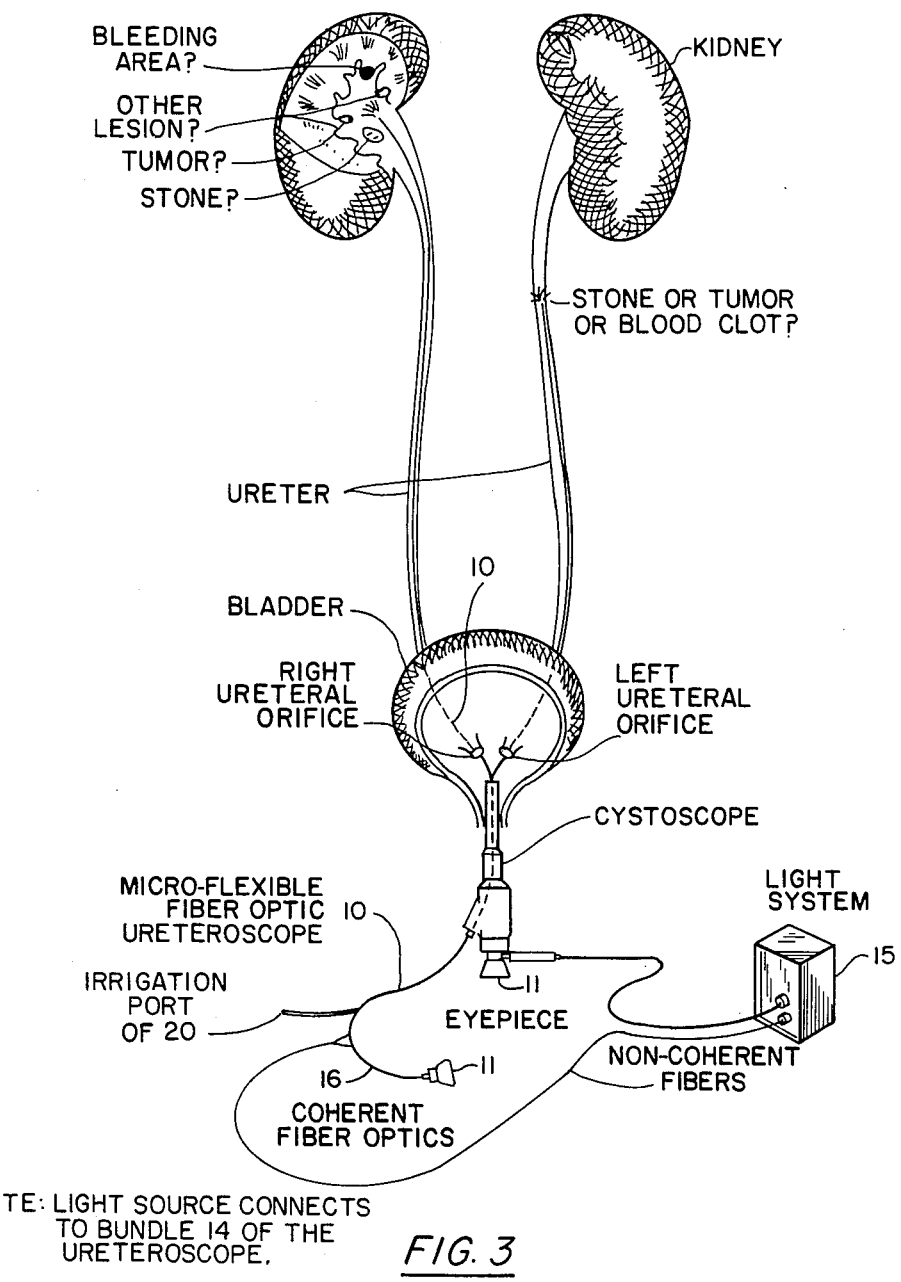
FIG. 3 depicts a schematic application of the preferred embodiment of this inventive concept having the capability for diagnosing and treating ureteral and renal disorders.

Referring now to the drawings, an imiproved endoscope 10 fabricated in accordance with the teachings of this inventive concept allows a viewer 11 to both observe for diagnostic purposes an object 12 and to perform treatment if the situation so allows.

The endoscope includes 60 to 80 centimeter length of a tubular-shaped casing 13. Preferably it is only a few mils thick and is made from a flexible, low-friction material such as a pvc or a self-lubricating polymethylene compound. It can be fabricated according to a variety of techniques; for example, extrusion, and has an outer diameter of no more than two millimeters.

A bundle of light carrying fibers 14 are adhered or fused together in a nearly semicircular cross-sectional configuration; although greater or lesser sector-shaped forms can also be used. The individual fibers have sixty micron diameters and have a glass index of 1.62 and a numerical aperture of 0.66 with a 41° half angle. These, arranged in a bundle, have proven acceptable for illuminating object 12 when a high intensity light source 15 is actuated. The high intensity source optionally is equipped with an infrared filter and projects over 100,000 foot candles through fiber bundle 14.

A bundle of glass fibers 16 coaxially extends the length of the endoscope to permit observation of object 12 by a viewer looking through an eyepiece 11a or to show the object on a TV monitor 17. If the latter application is used a videocon 18 or a CCD camera and suitable interconnecting circuitry is included. A suitable optical coupler is substituted for eyepiece 11a when a high energy laser 19 or ultrasound 19a is coupled for microsurgery; elaboration on these features will be discussed further below.

The observation bundle is a multitude of ten micron elements, each having a core of glass index equal to 1.62 and a numerical aperture 0.66 with a 41° half angle. The bundle is bonded or fused together to provide a sufficient resolution and acuity for an observer and also to function as a conduit for high energy coherent light from a laser 19 or ultrasound 19a.

The light carrying fiber bundle 14, the illuminating bundle, has a nearly semicircular cross-sectional area, see FIG. 2. This configuration is dimensioned to match the inner dimension of tubular casing 13 and expedites the thermal or mechanical bonding of the illuminating bundle within the tubular casing. An axially extending groove 14a is provided in the illuminating bundle and serves as a coaxially disposed channel in which observation bundle 16 is secured.

The observation bundle is shown as being a rectangular shape fitted into a correspondingly shaped groove; however, this particular design is not controlling. What controls the small size and, consequently, the effectiveness of this inventive concept is that the cooperation and the coaction of the two bundles and the tubular casing is such as to present an integral structure that defines a longitudinally extending duct 20 that runs the length of the endoscope. The longitudinal duct provides a conduit for the bi-directional flow of fluids, gases, smoke and by-products of microsurgery.

Since the tubular casing 13 has only a two millimeter diameter, the cross-sectional area of a typical observation bundle is about 1.0 mm and the cross-sectional area of the illumination bundle 14 is about 0.8 mm square, a one millimeter square lingitudinal duct is created by the described arrangement for ducting fluids. The illuminating bundle, the observation bundle and the interior of the tubular casing and the interior of the self-lubricating polymethylene casing cooperate to form a protuberance-free longitudinal duct 20. The duct carries injected dyes, radioisotopes and various fluids through it when a bulb 21 or other suitable metering device is actuated and can draw away collected fluids, smoke or other microsurgery by-products by laser 19 or ultrasound 19a at the object 12 when a vacuum is introduced by bulb 21.

As mentioned above, the laser source that provides coherent light or ultrasound 19a is directed through eyepiece 11a or a suitable coupler disposed thereat through observation bundle 16, lens 22 and onto the object undergoing treatment. The concentrated laser energy or ultrasound can be used for breaking up stones, evaporating a blood clot, microsurgery, tumor treatment, etc. Employing an infrared sensor in place of lens 22 would enable the detection and location of a blood clot through a vein. To burn the blood clot, a single element multi-mode fiber could be substituted for observation bundle 16 and a green argon laser 19 could be actuated for about five seconds to deliver 10–20 watts CW power. The residues, smoke, heat, etc. could be removed via longitudinally extending duct 20.

Looking to FIG. 3, a two millimeter diameter endoscope fabricated in accordance with the teachings of this inventive concept particularly lends itself toward the treatment of ureteral and renal disorders. A cystoscope is introduced into the bladder and an endoscope 10, fabricated in accordance with the teachings of this invention, is passed via the cystoscope, into the right ureteral orifice, through the right ureter and to the right renal pelvis and infundibular system (a similar pathway could be followed to the left kidney). Percipient medical observation would help establish the diagnosis and possibly avoid the risk, expense and convalescence of open surgery. In addition to the cost-effective, low-risk diagnosis provided by this invention, microsurgical, ultrasound, irrigated medication and laser treatment of benign and malignant lesions of the ureter and renal collection systems are possible. Introduction and withdrawal of the endoscope from the ureter and kidneys is at reduced discomfort and hazard to the patient and requires reduced or no anesthetic agents.

Obviously many modifications and variations of the present invention are possible in the light of the above teachings. It is therefore to be understood that within the scope of the appended claims the invention may be practiced otherwise than as specifically described.

What is claimed is:

1. An improved flexible endoscope having a reduced diameter throughout its entire length of insertion and flexibility for diagnosing and treating ureteral and renal disorders comprising:
    means extending the length of the endoscope for providing illumination having a sector-shaped cross-sectional configuration;
    means extending the length of the endoscope and adjacent the illumination providing means for permitting observation;
    an elongate flexible tubing extending the length of the endoscope and having an outer diameter dimension of two millimeters for encasing the illumination providing means and the observation permitting means and for defining a longitudinal fluid duct that completely fills the remainder of the elongate flexible tubing's interior, an outer surface of the illumination providing means has a rounded cross-sectional configuration shaped to contiguously accommodate an inner surface of the elongate flexible tubing and further has a coaxially disposed channel shaped to receive the observation permitting means and the two millimeter outer dimension of the elongate flexible tubing is small enough to pass into and through the ureter into the kidney without the need for ureteral dilation or without trauma.

2. An improved flexible endoscope according to claim 1 in which the illumination providing means is a first bundle of fiber optics having a semicircular cross-sectional configuration except for the coaxially disposed channel and the observation permitting means is a second fiber optic bundle having a cross-sectional area of 1.0 mm and the longitudinal fluid duct has a semicircular cross-sectional configuration except for a portion of the second fiber optic bundle.

3. An apparatus according to claim 2 in which the rounded outer surface of the first fiber optic bundle is adhered to the inner surface of the elongate flexible tubing and the second fiber optic bundle, is adhered in the coaxially disposed channel.

* * * * *